US00PP11858P2

(12) United States Plant Patent

Jessel, Jr.

(10) Patent No.: US PP11,858 P2

(45) Date of Patent: May 8, 2001

(54) CARNATION PLANT NAMED 'CFPC MARMALADE'

(75) Inventor: Walter H. Jessel, Jr., Gonzales, CA (US)

(73) Assignee: California Florida Plant Co, LP, Salinas, CA (US)

( * ) Notice: Subject to any disclaimer, the term of this patent is extended or adjusted under 35 U.S.C. 154(b) by 0 days.

(21) Appl. No.: 09/181,275

(22) Filed: Oct. 28, 1998

(51) Int. Cl.[7] ..... A01H 5/00

(52) U.S. Cl. ..... Plt./277

(58) Field of Search ..... Plt./277, 273, 272, Plt./276, 281

*Primary Examiner*—Bruce R. Campell
*Assistant Examiner*—Michelle Kizilkaya
(74) *Attorney, Agent, or Firm*—Christie, Parker & Hale, LLP

(57) ABSTRACT

A new variety of carnation plant producing orange picotee dark pink flowers.

1 Drawing Sheet

BACKGROUND OF THE INVENTION

The present invention relates to a new and distinct variety of carnation plant which was originated by me by crossing, as seed, an undistributed seedling identified as No. 930266 and as pollen parent, an undistributed seedling identified as No. 9304550. The varietal denomination of the new variety is 'CFPC Marmalade'.

SUMMARY OF THE INVENTION

Among the novel characteristics possessed by the new variety which distinguishes it is orange picotee dark pink flowers. When grown under glass in Salinas, Calif. in 4½ inch plastic pots, pinched plants are about 7½ inches tall and average flower diameter is 1½ inches, crown is about ⅞ inches. Foliage is about 3¼ inches long and about ⅜ inches wide. The new variety is mainly grown under greenhouse conditions but can be transplanted into a garden environment or patio container outdoors in areas protected from direct sun, such as plantings by walls and near shaded areas. It is believed that with regular watering and feeding, it is expected that new blooms will form and finish all year round. The new plant varies from the undistributed parent plants in that the seed parent, No. 930266 and the pollen parent, No. 9304550 are different in size and color.

Asexual reproduction by propagation by side shoot cuttings of the new variety as performed in Salinas, Calif., shows that the foregoing and other distinguishing characteristics come true to form and are established and transmitted through succeeding propagations.

BRIEF DESCRIPTION OF ILLUSTRATION

The accompanying illustration shows typical specimens of the vegetative growth and flowers of the new variety depicted in color as nearly true as it is reasonably possible to make the same in color illustration of this character.

DESCRIPTION OF THE NEW VARIETY

The following is a detailed description of my new variety, with color terminology in accordance with The Royal Horticultural Society Colour Chart (R.H.S.C.C.). The terminology used in color description herein refers to plate numbers in the aforementioned color chart. Phenotypical expression may vary depending upon varying environmental, seasonal and cultural conditions.

The information provided herein is based on observations of plants grown inside commercial greenhouses at Salinas, Calif. The height of plant and flower and foliage size are established as an average using standard commercial cultural practices.

Classification:

*Botanical.*—*Dianthus caryophyllus.*

*Commercial.*—Carnation, greenhouse type suitable for production as a pot spray.

1. Plant:
   - *Height.*—About 7½ inches.
   - *Growing habit.*—Herbaceous, semi-upright.
   - *Blooming habit.*—As a spray (pot), about 2 to 8 blooms per spray.
   - *Blooming season.*—Year round.
   - *Breaking action.*—About 7–8 per plant, pinching is required.
   - *Rooting time.*—About 18–19 days.
   - *Disease resistance.*—Good, typical for carnations.
2. Foliage:
   - *Color.*—Upper side: Near 137A. Lower side: Near 137A.
   - *Size.*—About 3¼ inches long, about ⅜ inches wide.
   - *Quantity.*—Numerous.
   - *Shape.*—Lanceolate.
   - *Texture.*—Smooth.
   - *Ribs.*—Central, keeled.
   - *Arrangement.*—Bi-lateral along stem.
   - *Stem color.*—Near 132B.
   - *Pedicel color.*—Near 137C.
3. Bud:
   - *Shape.*—Ovoid.
   - *Color.*—Near 139D.
   - *Length.*—About 1 inch.
   - *Diameter.*—About ½ inch.
4. Calyx:
   - *Number of bracts.*—About 5.
   - *Length.*—About 5/16 inch.
   - *Width.*—About ¼ inch.

*Color.*—Outside — near 139D. Inside — near 138D.
*Bursting/Splitting.*—Has not been observed.

5. Bloom:
*Shape.*—Round.
*Size.*—Diameter average: About 1½ inches. Depth average: About ⅞ inch.
*Borne.*—Terminally as a spray.
*Color.*—General tonality: Light orange, picotee dark pink. Upper side: Near 168D. Lower side: Near 165D. Center: Near 168D. Petal margins: Near 58B picotee pink edge.
*Fragrance.*—Slight.

6. Petals:
*Number.*—About 29.
*Outer petals.*—Length: About 1¼ inches. Width: About ⅝ inches.
*Central petals.*—Length: About 1 9/16 inches. Width: About ½ inch.
*Texture.*—Smooth.
*Form.*—Fan shaped.
*Appearance.*—Shiny.

7. Reproductive organs:
*Stamens.*—About 5–6.
*Anthers.*—About ⅛ inch, color near 159C.
*Filaments.*—About ½ inch, color whiter than 155D.
*Pistil.*—Number: 1. Color: Whiter than 155D. Length: About ⅔ inch.
*Stigma.*—Number: About 4 lobes. Color: Whiter than 155D.
*Ovary.*—Shape: Conical. Color: Base — near 155D. Body — near 145A. Apex — near 145A.
*Fertility.*—Female: Very good. Male: Fair.

I claim:

1. A new and distinct carnation plant of the variety substantially as shown and described.

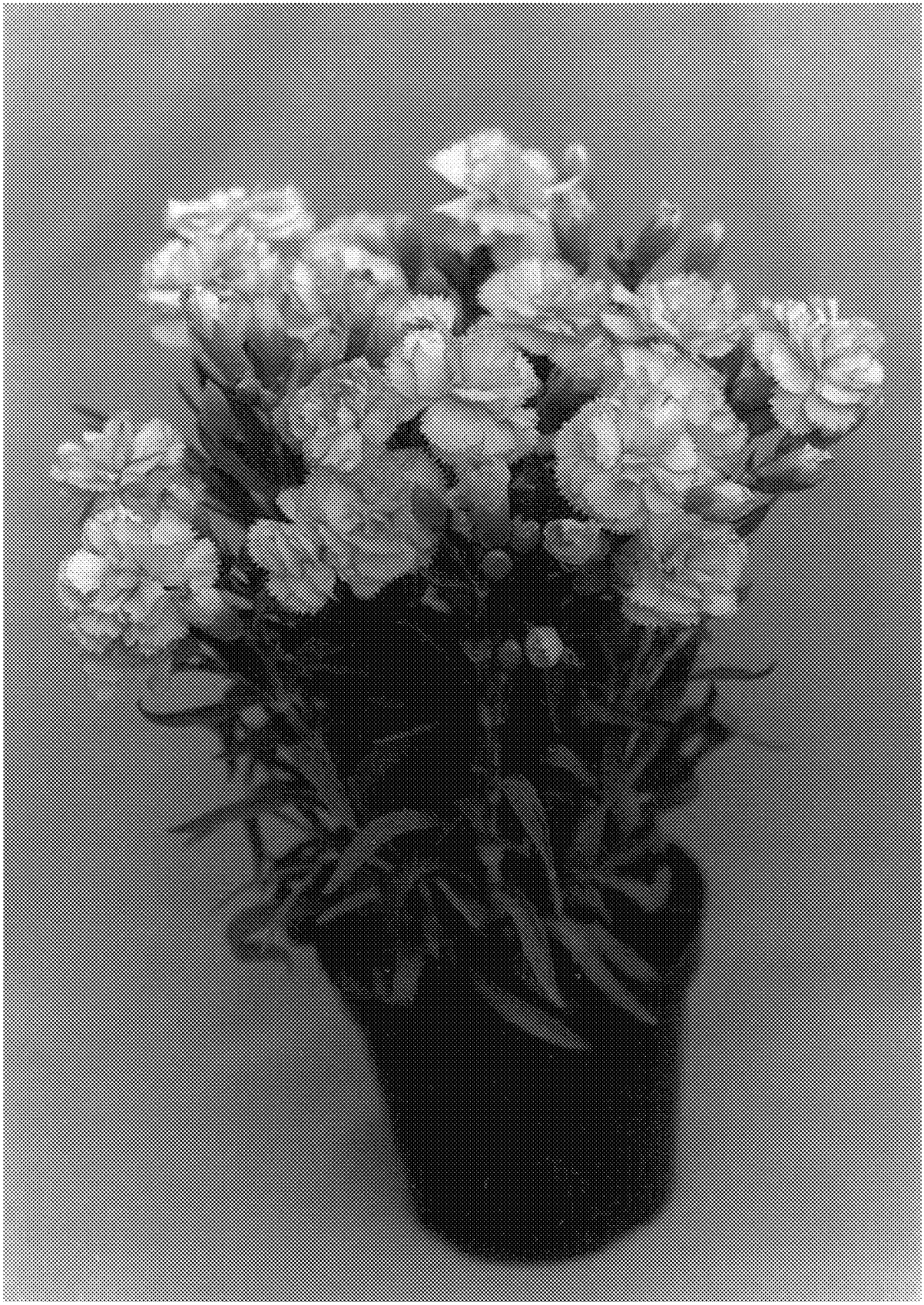

* * * * *